(12) United States Patent
Yanaki

(10) Patent No.: US 9,844,669 B2
(45) Date of Patent: Dec. 19, 2017

(54) COSMETIC IONTOPHORESIS SYSTEM

(75) Inventor: Jamal S. Yanaki, Salt Lake City, UT (US)

(73) Assignee: ActivaDerm, Inc., West Valley City, UT (US)

(*) Notice: Subject to any disclaimer, the term of this patent is extended or adjusted under 35 U.S.C. 154(b) by 652 days.

(21) Appl. No.: 12/737,327

(22) PCT Filed: Jul. 2, 2008

(86) PCT No.: PCT/US2008/008215
§ 371 (c)(1),
(2), (4) Date: Mar. 9, 2011

(87) PCT Pub. No.: WO2010/002363
PCT Pub. Date: Jan. 7, 2010

(65) Prior Publication Data
US 2011/0160639 A1  Jun. 30, 2011

(51) Int. Cl.
*A61N 1/30* (2006.01)
*A61N 1/04* (2006.01)

(52) U.S. Cl.
CPC .............. *A61N 1/30* (2013.01); *A61N 1/044* (2013.01); *A61N 1/0448* (2013.01)

(58) Field of Classification Search
CPC ........ A61N 1/30; A61N 1/0448; A61N 1/044; A61N 1/325

USPC .............................. 604/20, 501, 891.1, 892.1
See application file for complete search history.

(56) References Cited

U.S. PATENT DOCUMENTS

| | | | |
|---|---|---|---|
| 4,406,658 A | * | 9/1983 | Lattin et al. .................... 604/20 |
| RE32,724 E | * | 8/1988 | Cartmell ....................... 600/392 |
| 5,295,482 A | * | 3/1994 | Clare et al. ................... 600/385 |
| 2005/0148996 A1 | * | 7/2005 | Sun et al. ..................... 604/501 |

* cited by examiner

*Primary Examiner* — Imani Hayman
*Assistant Examiner* — Nilay Shah

(57) ABSTRACT

Iontophoretically administering a cosmetic agent requires an active electrode and a return electrode secured to the skin (150). The active electrode includes a flexible biocompatible substrate (20, 170) having a therapeutic face (106, 206) configured for disposition toward the skin (150) and an exterior periphery (32, 182) shaped to facilitate conformance of the substrate (20, 170) to the skin (150) over an intended treatment region. A flexible electrically conductive layer (110, 210) is disposed on the therapeutic face (106, 206). The side of the conductive layer (110, 210) opposite from the substrate (20, 170) defines a driving face (120, 220) to which is affixed an electrically conductive adhesive matrix (82, 192) comprised of a material capable of repeatedly releasably securing the active electrode to the skin (150) through an applied solution (156, 158) of the cosmetic agent. A power source (76, 186) electrically connectable to the return electrode and to the conductive layer (110, 210) of the active electrode causes migration of the cosmetic agent away from the adhesive matrix (82, 192) into the skin (150).

7 Claims, 8 Drawing Sheets

COSMETIC IONTOPHORESIS SYSTEM

BACKGROUND

A. Field of the Invention

The present invention relates to the administration of a cosmeceutical preparation to the skin of a subject. More particularly, the present invention relates to the transcutaneous delivery of a cosmetic agent in solution using iontophoresis.

B. Background of the Invention

As used hereinafter, the expression "cosmetic agent" refers to substances administered to the skin of a subject to alter appearance, to enhance vitality, or to otherwise facilitate subsequent cosmetic undertakings. Thus, the expression "cosmetic agent" includes skin numbing substances that reduce skin sensation in preparation for aggressive cosmetic procedures, such as surface abrasion, hair removal, or tattoo erasure.

One method for delivering a cosmetic agent in a cosmeceutical solution into the skin of a subject involves coating the skin of the subject over an intended treatment region with the cosmeceutical solution and allowing the cosmetic agent in the solution to penetrate the skin by osmosis and by any related spontaneously occurring mass transport phenomena.

If a cosmetic agent in a cosmeceutical solution possesses ionic properties, then a more sophisticated technique for delivering the cosmetic agent uses electrical energy to induce the cosmetic agent to penetrate the skin. This is called iontophoresis.

Iontophoresis affords enhanced control over the rate of delivery of the cosmetic agent and over the depth of the penetration by the cosmetic agent into the skin of the subject. Additionally, iontophoresis can induce larger molecules of a cosmetic agent to penetrate the skin than would be possible by merely coating the skin with a solution containing that cosmetic agent.

Iontophoresis involves the application of an electromotive force to drive a cosmetic agent into the skin. An iontophoretic system includes two electrodes that engage the surface of the skin at respective locations that are distanced from each other. One of these electrodes is positioned with a supply of the cosmetic agent on the skin within the intended treatment region; the other is positioned on the skin beyond the intended treatment region.

During iontophoresis, direct electrical current is used to cause ions of the cosmetic agent to cross the surface of the skin and to diffuse into underlying tissue. The surface of the skin is not broken by this administration of the cosmetic agent. When conducted within appropriate parameters, the sensations experienced by a subject during the delivery of the cosmetic agent in this manner are not unpleasant.

The direct current employed in an iontophoresis system may be obtained from a variety of electrical power sources. These include diminutive disposable batteries carried on one of the electrical contacts used in the iontophoresis system, paired regions of contrasting galvanic materials that when coupled by a fluid medium produce minute electrical currents, and electrical hardware powered by sizable consumable or rechargeable batteries or through electrical cord interconnection to a wall socket.

The bulk, weight, and cost of electrical hardware powered by sizable consumable or rechargeable batteries or through electrical cord interconnection to a wall socket necessitate that such electrical hardware be configuration as equipment distinct from either of the electrical contacts that are applied directly to the skin to administer a cosmetic agent iontophoretically. Accordingly, power sources that are driven by sizable consumable or rechargeable batteries or through electrical cord interconnection to a wall socket limit the mobility of the subject during the time that treatment is in progress. Still, such power sources are advantageously robust and are, therefore, capable of effecting the iontophoretic delivery of a given quantity of cosmetic agent at a faster rate than is available using other sources of direct current.

A flow of electrical current requires an uninterrupted, electrically-conductive pathway from the positive pole of a power source to the other, negative pole thereof. Living tissue is made up primarily of fluid and is, therefore, a conductor of electrical current. In an iontophoretic circuit, the opposite poles of a power source are electrically coupled to respective, separated contact locations on the skin of the subject. The difference in electrical potential created by the power source between those contact locations causes a movement of electrons and electrically charged ions through the skin between the contact locations In an iontophoretic delivery system, the polarity of the net overall electrical charge on dissolved molecules of a cosmetic agent determines the nature of the electrical interconnection that must be effected between the power source that is used to drive the system and the supply of the cosmetic agent that is positioned on the skin at one of the contact locations used by the system. A positively charged cosmetic agent on the skin of the subject is coupled to the positive pole of the power source. Correspondingly, a negatively charged cosmetic agent on the skin of the subject must be coupled to the negative pole of such a power source. Examples of common iontophoretically administrable cosmetic agents in each category of polarity are listed in the table below.

| Positive Polarity Cosmetic Agents | Negative Polarity Cosmetic Agents |
|---|---|
| Lidocaine | Acetic acid |
| Vitamin A | Retinyl palmitate |
| Tocopheryl acetate | Tocopherol |
| | Glucoside |
| | Mandelic acid |

An iontophoretic circuit for driving a cosmetic agent into the skin is established by coupling the appropriate pole of the power source through the cosmetic agent on the skin at the treatment region where the cosmetic agent is to be administered. Simultaneously, the other pole of the power source is coupled to a location on the skin of the subject that is distanced from the treatment region. The coupling of each pole of the power source is effected by the electrical connection of each pole to a respective of the two electrodes of the iontophoresis system. The electrode at the treatment region is referred to as the active electrode; the electrode at the contact location on the skin distanced from the treatment region is referred to as the return electrode.

An iontophoresis system does not require intensive skin site sanitation to avoid infections. Patches and the other equipment used in iontophoresis do not interact with bodily fluids and, accordingly, need not be disposed as hazardous biological materials following use. With some exceptions, no pharmacologically significant portion of a cosmetic agent delivered iontophoretically becomes systemically distributed. Rather, a cosmetic agent delivered iontophoretically remains localized in the tissue at the site of administration.

The dosage of a cosmetic agent delivered iontophoretically is conveniently and accurately measured by monitoring the amount and the duration of the electrical current flowing during the administration. With electrical current being measured in amperes, and with time being measured in minutes, the dosage of a cosmetic agent given transcutaneously is given in units of ampere-minutes. Due to the minute quantities of cosmetic agent required in iontophoresis, the dosage of a cosmetic agent administered by iontophoresis is frequently specified in the smaller unit of milliampere-minutes.

SUMMARY OF THE INVENTION

According to teachings of the present invention, an active electrode patch is provided for use in iontophoretically administering into the skin of a subject a cosmetic agent in a cosmeceutical solution on the skin of the subject.

On one side of a flexible biocompatible substrate is a therapeutic face of the substrate that is configured for disposition toward the skin of the subject. The substrate has an exterior periphery shaped to facilitate the conformance of the therapeutic face of the substrate with the skin of the subject over an intended treatment region in which the cosmetic agent is to be induced electrically to migrate. A flexible electrically conductive layer is disposed on the therapeutic face of the substrate. The surface of the side of the conductive layer opposite from the substrate defines a driving face of the conductive layer.

An electrically conductive adhesive matrix is affixed to the driving face of the conductive layer. The adhesive matrix is made from a material that is capable of repeatedly releasably securing the active electrode patch to the skin of the subject through a coating of the cosmeceutical solution. The material of the adhesive matrix may be an adhesive hydrogel, such as a linked polymer acrylic adhesive.

According to one aspect of the present invention, in an active electrode patch as described above, the exterior periphery of the substrate is provided with an exterior fitting slit formed through the substrate and extending from the exterior periphery thereof into the substrate. The exterior fitting slit permits the portions of the substrate adjacent to and on opposite sides of the exterior fitting slit at the exterior periphery to be overlapped, thereby enhancing the conformity of the exterior periphery of the substrate to the skin of the subject about the treatment region.

According to another aspect of the present invention, in an active electrode patch as described above, an aperture is formed through the substrate. The aperture is defined by a continuous interior periphery of the substrate. The interior periphery that defines the aperture is shaped to facilitate the conformance of the therapeutic face of the substrate to the skin of the subject interior of the treatment region. The interior periphery of the substrate is provided with an interior fitting slit formed through the substrate and extending from the interior periphery into the substrate. The interior fitting slit permits the portions of the substrate adjacent to and on opposite sides of the interior fitting slit at the interior periphery to be overlapped, thereby enhancing the conformity of the interior periphery of the substrate to the skin of the subject interior of the treatment region.

According to yet another aspect of the present invention, in an active electrode patch as described above, an adjustment slit is formed through the substrate between the exterior periphery and any interior periphery thereof. The adjustment slit permits the portions of the substrate adjacent to and on opposite sides of the adjustment slit between the exterior periphery and the interior periphery to be overlapped, thereby enhancing the conformity of the substrate between the exterior periphery and the interior periphery to the skin of the subject at the treatment region.

Further, teachings of the present invention provide an active iontophoresis patch for use in iontophoretically administering into the skin of a subject a cosmetic agent in a cosmeceutical solution coating the skin of the patient.

A flexible biocompatible substrate has on one side thereof a therapeutic face configured for disposition toward the skin of the subject. The substrate includes a return electrode region and separated therefrom an active electrode region that is shaped to facilitated conformance of the therapeutic face of the substrate to the skin of the subject over an intended treatment region. A flexible first electrically conductive layer is disposed on the therapeutic face of the substrate in the active electrode region, while a second electrically conductive layer is disposed on the therapeutic face of the substrate in the return electrode region. The surface of the side of the first electrically conductive layer opposite from the substrate defines a driving face of the first electrically conductive layer, and the surface of the side of the second electrically conductive layer opposite from the substrate defines a receiving face of the second electrically conductive layer.

An electrically conductive adhesive matrix is affixed to the driving face of the first conductive layer, while an electrically conductive adhesive covers the receiving face of the second electrically conductive layer. The adhesive matrix and the electrically conductive adhesive are each made from materials that are capable of repeatedly releasably securing the active electrode region and the return electrode region, respectively, to the skin of the subject. In the case of the active electrode region, this occurs notwithstanding the presence on the skin of the subject of a coating of the cosmeceutical solution. The material of the adhesive matrix may be an adhesive hydrogel, such as a linked polymer acrylic adhesive. The material of the electrically conductive adhesive may be identical to that of the adhesive matrix.

A power source carried on the substrate is electrically coupled with the first electrically conductive layer and with the second electrically conductive layer. In this manner, the power source causes migration into the skin of the subject away from the adhesive matrix of the cosmetic agent in the cosmeceutical solution on the skin of the subject. Typically, such a power source takes the form or one or more consumable batteries that are located on either side of the substrate. An active iontophoresis patch thusly configured is completely self-contained, and being a unitary structure offers a fully integrated approach to the administration of a cosmetic agent into the skin of a subject. Alternatively, the substrate carries electrical connections to the first electrically conductive layer and to the second electrically conductive layer, and an external power source is coupled to these electrical connections as needed.

In such a light, the teachings of the present invention provide in effect a system for iontophoretically administering into the skin of a subject a cosmetic agent in a cosmeceutical solution on the skin of the subject. Such a system includes an active electrode patch as described briefly at the commencement of this section, a return electrode releasably securable in an electrically-coupled relationship to the skin of the subject exterior of an intended treatment region, and a power source electrically connectable with the return electrode and through the active electrode patch to the skin of the subject. The power source causes the migration of the cosmetic agent in the cosmeceutical solution into the skin of the subject and away from the active electrode patch.

The present invention includes a method for iontophoretically administering a cosmeceutical solution to the skin of a subject. That method includes the steps of coating the skin of the subject over an intended treatment region with a cosmeceutical solution containing a cosmetic agent, securing an active electrode patch as described briefly at the commencement of this section to the treatment region of the skin after the step of coating, electrically connecting a power source through the active electrode patch to the skin of the subject, and removing the active electrode patch from the skin of the subject at the conclusion of a predetermined therapy period.

The method of the present invention may continue thereafter through the steps of cleaning the surface of the active electrode patch that had previously engaged the skin of the subject and then of repeating in order, first, the step of coating the skin of the subject, and second, the step of securing the active electrode patch to the treatment region of the skin.

BRIEF DESCRIPTION OF THE DRAWINGS

The manner in which the advantages and objects of the invention are obtained will be understood by a more particular description of the invention rendered by reference to specific embodiments thereof that are illustrated in the appended drawings. Understanding that these drawings depict only typical embodiments of the invention and are not therefore to be considered limiting of the scope thereof, the invention will be described and explained with additional specificity and detail through the use of the accompanying drawings in which.

DETAILED DESCRIPTION OF EMBODIMENTS OF THE INVENTION

In the following description, for purpose of explanation, specific details are set forth in order to provide an understanding of the invention. Nonetheless, the present invention may be practiced without some or all of these details. The embodiments of the present invention, some of which are described below, may be incorporated into a number of elements of cosmetic systems additional to the cosmetic systems in which those embodiments are by way of necessity illustrated herein. Structures and devices shown in the figures illustrate merely exemplary embodiments of the present invention, thereby to facilitate discussion of teachings of the present invention. Thus, the details of the structures and devices shown in the figures are not supplied herein to serve detractors as instruments with which to mount distracting denials of the existence of broad teachings of present invention that are manifest from this specification taken as a whole.

Connections between components illustrated in the figures are not limited to direct connections between those components. Rather, connections between such components may be modified, reformatted, or otherwise changed to include intermediary components without departing from the teachings of the present invention.

References in the specification to "one embodiment" or to "an embodiment" mean that a particular feature, structure, characteristic, or function described in connection with the embodiment being discussed is included in at least one embodiment of the present invention. Furthermore, the use of the phrase "in one embodiment" in various places throughout the specification is not necessarily a reference in each instance of use to any single embodiment of the present invention.

Figure 1:
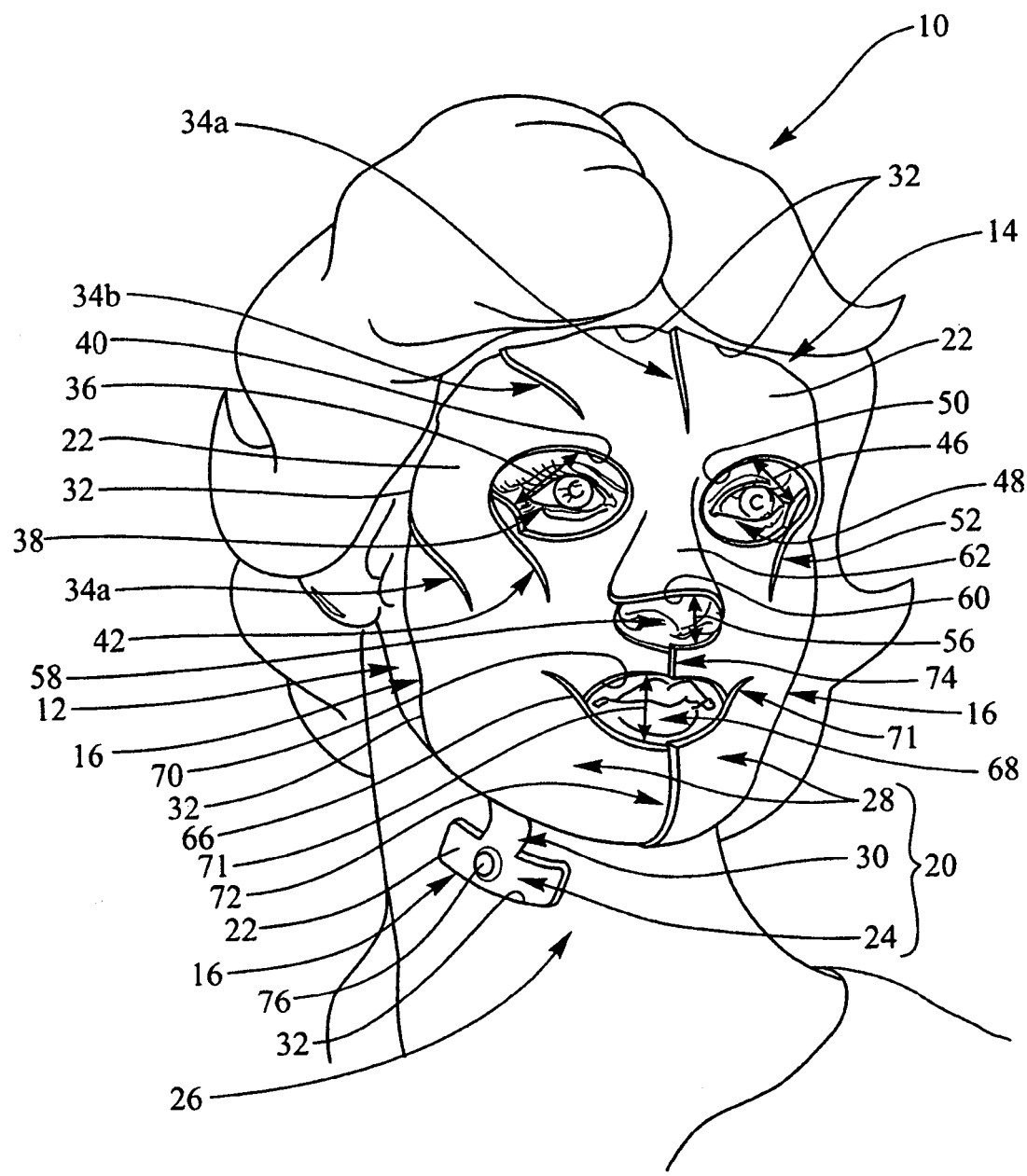
FIG. 1 is a perspective view of a first embodiment of an active iontophoresis patch incorporating teachings of the present invention being worn by a subject during the administration of a cosmetic agent to the skin of the face thereof.

FIG. 1 depicts a subject 10 during the administration of a cosmetic agent to the skin of the face 12 thereof. Toward that end, subject 10 is wearing over the substantial entirety of face 12 thereof a first embodiment of an active iontophoresis cosmetic agent administration system 14 that incorporates teachings of the present invention. While so doing, subject 10 is nonetheless able to engage in activity, because administration system 14 is entirely self-contained, not being supplied with direct current from any external power source.

Administration system 14 takes the form of a fully-integrated, active iontophoresis patch 16 that is secured to the skin in an intended treatment region on face 12 of subject 10 for the duration of a predetermined treatment period. The length of the treatment period during which iontophoresis patch 16 must be worn is determined by the rate at which iontophoresis patch 16 delivers a cosmetic agent through the skin of subject 10 and the total dose of the cosmetic agent that is to be administered. The cosmetic agent is contained in a cosmeceutical solution that is applied as a coating to the skin of the intended treatment region before iontophoresis patch 16 is secured thereto.

According to one aspect of the present invention, iontophoresis patch 16 is so constructed as to be repeatedly releasable securable to the skin of subject 10. Thus, iontophoresis patch 16 can be repositioned on the skin of subject 10 as needed, or iontophoresis patch 16 can be removed at the end of the predetermined treatment period, washed, and stored until required for a subsequent treatment session involving subject 10. Once the treatment region has again been coated with a cosmeceutical solution containing the same, or even a different, cosmetic agent, iontophoresis patch 16 is again releasably secured to the skin of the intended treatment region for a second predetermined treatment period.

While it is not necessary according to teachings of the present invention that such steps be repeatable indefinitely, it is contemplated using the materials and the constructions disclosed hereinafter that a cosmetic iontophoresis patch, such as iontophoresis patch 16, be reusable at least on a plurality of occasions, possibly in a range of from 2 to 15 occasions, and more narrowly in a range of from 5 to 10 occasions.

Iontophoresis patch 16 is a comparatively thin structure having a layered construction that will be explored in detail subsequently. Nonetheless, it can be noted here that iontophoresis patch 16 includes an irregularly-shaped, flexible biocompatible substrate 20 having an outer face 22 that forms the surface of iontophoresis patch 16 visible in FIG. 1. Substrate 20 is substantially coextensive with the maximum extent of iontophoresis patch 16 and thus serves as a unifying structure for the balance of the elements of iontophoresis patch 16.

When not secured in conformance to the skin of subject 10 during use, iontophoresis patch 16 is capable of disposition for storage in an entirely flat, planar configuration, or of being curled back upon itself into a roll. While susceptible to folding, sharp bending of iontophoresis patch 16 is not recommended, as doing so is likely over time to degrade the layered construction thereof and, consequently, to reduce the number of occasions on which iontophoresis patch 16 can reliably be put to use.

Substrate 20 includes a relatively small return electrode region 24 that is shown in FIG. 1 to be releasable secured to the neck 26 of subject 10 at a distance from the intended treatment region to which a cosmetic agent is intended to be transcutaneously administered. Substrate 20 also includes a significantly larger active electrode region 28 that is separated from return electrode region 24 by a narrow bridge portion 30 of substrate 20. Active electrode region 28 of substrate 20 is shaped to enable iontophoresis patch 16 to closely conform to the skin of subject 10 over an intended treatment region as irregular as the substantial entirety of face 12 of subject 10.

For example, substrate 20 has an exterior periphery 32 in active electrode region 28 thereof that is particularly shaped to facilitate the conformance of substrate 20 to the skin of the subject over the intended treatment region. In addition, as seen in FIG. 1, exterior periphery 32 of said substrate 20 includes a number of exterior fitting slits 34*a*, 34*b*, and 34*c* that are formed through substrate 20 and that extend from exterior periphery 32 into substrate 20. The portions of substrate 20 adjacent to and on opposite sides of exterior fitting slits 34*a*, 34*b*, and 34*c* at exterior periphery 32 can be overlapped as shown in FIG. 1 to enhance the close conformity of exterior periphery 32 of substrate 20 to the skin of subject 10 about the intended treatment region.

In addition, apertures are formed through substrate 20 wherever an area internal to the intended treatment region is desired to be excluded from being contacted by iontophoresis patch 16. Each such aperture is defined by a corresponding, continuous interior periphery of substrate 20, and each such interior periphery is shaped to further facilitate conformance of substrate 20 to the skin of subject 10 interior of the treatment region.

Thus, a right eye aperture 36 is formed through substrate 20 at a position therein that is calculated to overlie the right eye 38 of subject 10, thereby to accommodate that opening in the skin of subject 10, when iontophoresis patch 16 is being worn. Right eye aperture 36 is defined by an interior periphery 40 of substrate 20 that is so shaped as to enhance the conformity of substrate 20 to the skin of subject 10 about right eye 38 thereof. Interior periphery 40 of substrate 20 includes an interior fitting slit 42 that is formed through substrate 20 extending from interior periphery 40 into substrate 20. The portions of substrate 20 adjacent to and on opposite sides of interior fitting slit 42 can be overlapped as shown in FIG. 1 to enhance the close conformity of interior periphery 40 of substrate 20 to the skin of subject 10 interior of the intended treatment region at the outside corner of right eye 28.

Similarly, a left eye aperture 46 is formed through substrate 20 at a position therein that is calculated to overlie the left eye 48 of subject 10, thereby to accommodate that opening in the skin of subject 10, when iontophoresis patch 16 is being worn. Left eye aperture 46 is defined by an interior periphery 50 of substrate 20 that is so shaped as to enhance the conformity of substrate 20 to the skin of subject 10 about left eye 48 thereof. Interior periphery 50 of substrate 20 includes an interior fitting slit 52 that is formed through substrate 20 extending from interior periphery 50 into substrate 20. The portions of substrate 20 adjacent to and on opposite sides of interior fitting slit 52 can be overlapped as shown in FIG. 1 to enhance the close conformity of interior periphery 50 of substrate 20 to the skin of subject 10 interior of the intended treatment region at the outside corner of left eye 28.

A nose aperture 56 is formed through substrate 20 at a position therein that is calculated to overlie the nose 58 of subject 10, thereby to accommodate that projecting portion of the body of subject 10, when iontophoresis patch 16 is being worn. Nose aperture 56 defines an interior periphery 60 of substrate 20 that is so shaped as to enhance the conformity of substrate 20 to the skin of subject 10 about nose 58 and to produce a flap 62 that rests upon the bridge of nose 58.

In the planar disposition of iontophoresis patch 16 discussed subsequently in relation to FIG. 2, nose aperture 56 assumes the form of a slit in substrate 20, rather than any opening therethrough. Nonetheless, the three-dimensional disposition of iontophoresis patch 16 on face 12 of subject 10 in FIG. 1 causes a true opening to appear at nose aperture 56. Thus, interior periphery 60 of nose aperture 56 encompasses the opposing, abutting surfaces of the slit illustrated in FIG. 2 at the position of nose aperture 56.

The interior periphery of substrate 20 at an aperture, such as nose aperture 56, may be provided with one or more interior fitting slits of the type illustrated as being associated with interior periphery 40 at right eye aperture 36, with interior periphery 50 at left eye aperture 46, and with interior periphery 50 at mouth aperture 66. Any interior fitting slit associated with interior periphery 60 at nose aperture 56 would permit the portions of substrate 20 adjacent to and on opposite sides of the interior fitting slit to be overlapped to enhance the close conformity of interior periphery 60 of substrate 20 to the skin of subject 10 interior of the intended treatment region at nose 58.

A mouth aperture 66 is formed through substrate 20 at a position therein that is calculated to overlie the mouth 68 of subject 10, thereby to accommodate that opening in the skin of subject 10, when iontophoresis patch 16 is being worn. Mouth aperture 66 is defined by an interior periphery 70 of substrate 20 that is so shaped as to enhance the conformity of substrate 20 to the skin of subject 10 about mouth 68. Interior periphery 70 of substrate 20 at mouth aperture 66 includes a pair of interior fitting slits 71. Each of interior fitting slits 71 permits the portions of substrate 20 at mouth aperture 66 adjacent to and on opposite sides of each of interior fitting slits 71 to be overlapped, thereby enhancing the close conformity of interior periphery 70 of substrate 20 to the skin of subject 10 interior of the intended treatment region at each of the corners of mouth 68.

An exterior adjustment slit 72 is formed through substrate 20 between exterior periphery 32 thereof and interior periphery 70 at mouth aperture 66. Exterior adjustment slit 72 permits the portions of substrate 20 adjacent to and on opposite sides of exterior adjustment slit 72 to be overlapped as needed during use, thereby enhancing the conformity of substrate 20 between exterior periphery 32 thereof and mouth aperture 66 to the skin of the lower lip and the chin of subject 10.

An interior adjustment slit 74 is formed through substrate 20 between interior periphery 70 at mouth aperture 66 and interior periphery 60 at nose aperture 56. Interior adjustment slit 74 permits the portions of substrate 20 adjacent to and on opposite sides of interior adjustment slit 74 to be overlapped as needed during use, thereby enhancing the conformity of substrate 20 between mouth aperture 66 and nose aperture 56 to the skin of the upper lip of subject 10.

A power source 76 is carried on return electrode region 24 interior of the exterior periphery 78 of substrate 20. Power source 76 is electrically coupled with elements of iontophoresis patch 16 not visible in FIG. 1 so as to cause a cosmetic agent in a cosmeceutical solution on the skin of subject 10 beneath active electrode region 28 of substrate 20 to migrate away from iontophoresis patch 16 into the skin of subject 10.

For most cosmetic applications, the output voltage produced by a power source, such as power source 76, ranges from about 1.00 volt to about 15.00 volts. Alternatively, the output voltage produced by power source 76 ranges from about 2.00 volts to about 9.00 volts, or from about 3.00 volts to about 6.00 volts. Power source 76 is, by way of example, capable of delivering a direct current of about 3 volts potential. Power source 76 may be a single battery of higher or lower output potential, or power source 76 may be a plurality of series-connected batteries of equal or unequal output potential.

In general, the greater the output voltage produced by a mobile power source, such as power source 76 associated with an active cosmetic transdermal patch, the larger will be the skin current $I_S$ produced by that patch, and the shorter will be the treatment period required to enable that patch to administer any predetermined total amount of cosmetic agent. While such a result is salutary relative to minimizing the time during which a subject is required to be encumbered by wearing the patch, the larger the skin current $I_S$ produced by a patch, the greater the likelihood that a wearer of the patch will experience uncomfortable sensations, or even pain, during treatment. Accordingly, an unavoidable tradeoff exists between the desirable ends of comfort and of speedy treatment. Lower levels of power source output are calculated to increase subject comfort and to improve the likelihood that a subject will be willing to successfully complete a prescribed course of treatment, once that course of treatment has been undertaken.

Figure 2:
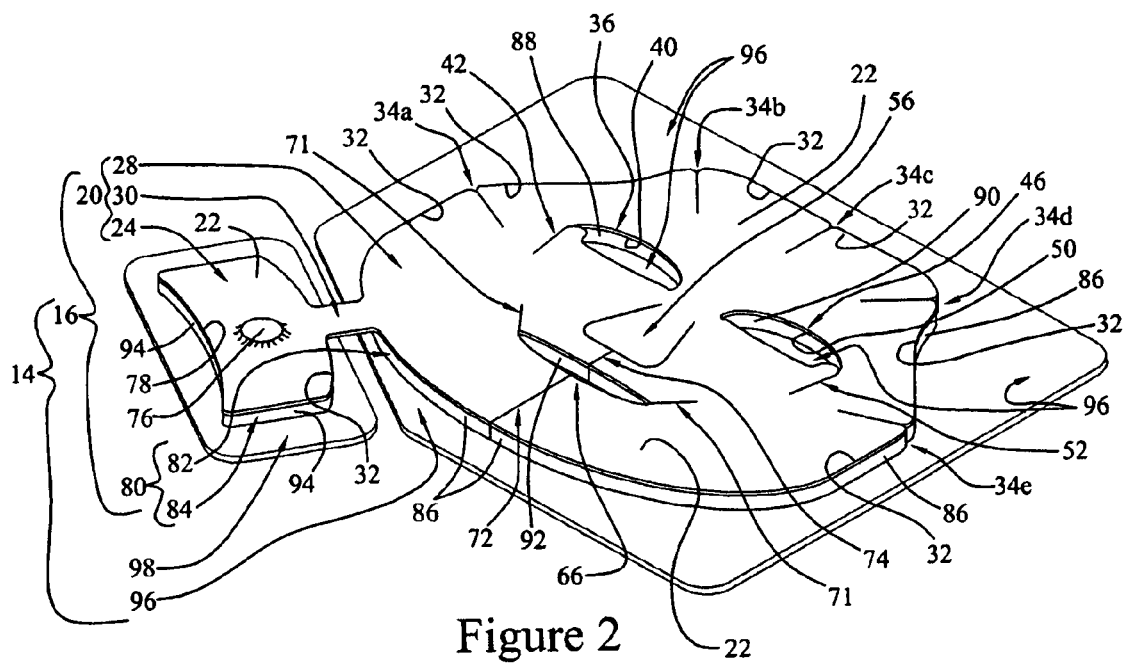
FIG. 2 is a perspective view in planar disposition of the active iontophoresis patch of FIG. 1 carrying on the active electrode region of the substrate of the patch a large release liner and on the return electrode region of the substrate of the patch a small release liner.

FIG. 2 is a perspective view of iontophoresis patch 16 of FIG. 1 in a planar disposition, the condition in which iontophoresis patch 16 is marketed and commonly stored between uses. The layered structure of iontophoresis patch 16 is there more fully appreciated.

Substrate 20 is depicted as an outer skin for a relatively thicker, electrically conductive, adhesive matrix 80. Adhesive matrix 80 is affixed to the side of substrate 20 opposite from outer face 22 thereof. Adhesive matrix 80 includes an extensive active electrode segment 82 that is carried on active electrode region 28 of substrate 20 and a return electrode segment 84 that is carried on return electrode region 24 of substrate 20. No portion of adhesive matrix 80 is affixed to bridge portion 30 of substrate 20. As a result, active electrode segment 82 of adhesive matrix 80 is electrically isolated from return electrode segment 84 of adhesive matrix 80 in the plane of adhesive matrix 80.

An exterior side edge surface 86 of active electrode segment 82 of adhesive matrix 80 coincides with exterior periphery 32 of substrate 20 in active electrode region 28 thereof. In FIG. 2, exterior side edge surface 86 of active electrode segment 82 is seen extending from exterior fitting slit 34*d* through exterior fitting slit 34*e* and exterior adjustment slit 72 to bridge portion 30 of substrate 20. A first interior side edge surface 88 of adhesive matrix 80 can be seen at right eye aperture 36 of substrate 20, while a second interior side edge surface 90 is presented at left eye aperture 46 of substrate 20. A third interior side edge surface 92 of adhesive matrix 80 appears at mouth aperture 66 on either side of interior adjustment slit 74. An exterior side edge surface 94 of return electrode segment 84 is revealed at exterior periphery 78 of substrate 20 in return electrode region 24 thereof.

Without departing from teachings of the present invention, iontophoresis patch 16, may omit some or all of fitting features, such as exterior fitting slits 34*a*, 34*b*, 34*c*, 34*d*, 34*e*, interior fitting slits 42, 52, exterior adjustment slit 72, and interior adjustment slit 74, or additional such fitting features may be incorporated thereinto. Nonetheless, the slit of each such fitting feature extends not just through substrate 20, but also through adhesive matrix 80 as well. In this manner the entire layered structure of iontophoresis patch 16 on either side of the slit of each fitting features can be overlapped as needed in the manner described previously and depicted in FIG. 1.

One face of adhesive matrix 80 is permanently secured to substrate 20, but the opposite, exposed face of adhesive matrix 80 is capable of being repeatedly secured to and removed from the skin of subject 10. Thus, it is adhesive matrix 80 that actually retains iontophoresis patch 16 on face 12 of subject 10 in FIG. 1.

When not in use, the exposed face of active electrode segment 82 of adhesive matrix 80 is protected by a selectively repeatedly removable, large release liner 96. The presence of large release liner 96 on the exposed face of active electrode segment 82 of adhesive matrix 80 facilitates the handling and storage of iontophoresis patch 16. Similarly, return electrode segment 84 of adhesive matrix 80 is protected by a distinct, selectively repeatedly removable, small release liner 98. Alternatively, both large release liner 96 and small release liner 98 can be incorporated into a comprehensive, one-piece release liner of any convenient shape.

Large release liner 96 and small release liner 98 are removable from iontophoresis patch 16 independently. Thus, large release liner 96 can be removed from active electrode segment 82 of adhesive matrix 80, while small release liner 98 is remains protecting return electrode segment 84 of adhesive matrix 80. In that condition, return electrode segment 84 of adhesive matrix 80 on active electrode region 28 of substrate 20 can be securely fitted into conformity with the skin of a subject over an intended treatment region, while the portion of iontophoresis patch 16 at return electrode region 24 of substrate 20 is precluded by small release liner 98 from catching onto surfaces in any unintended manner.

When the portion of iontophoresis patch 16 at active electrode region 28 of substrate 20 has been properly positioned, and treatment is to be commenced, small release liner 98 is removed from return electrode segment 84 of adhesive matrix 80. The portion of iontophoresis patch 16 at return electrode region 24 is then made to engage the skin of the subject. At that time, active iontophoresis actually commences. Small release liner 98 thus also functions to maintain return electrode segment 84 of adhesive matrix 80 in electrical isolation, until such time as the energy of power source 76 is actually needed.

Figure 3:
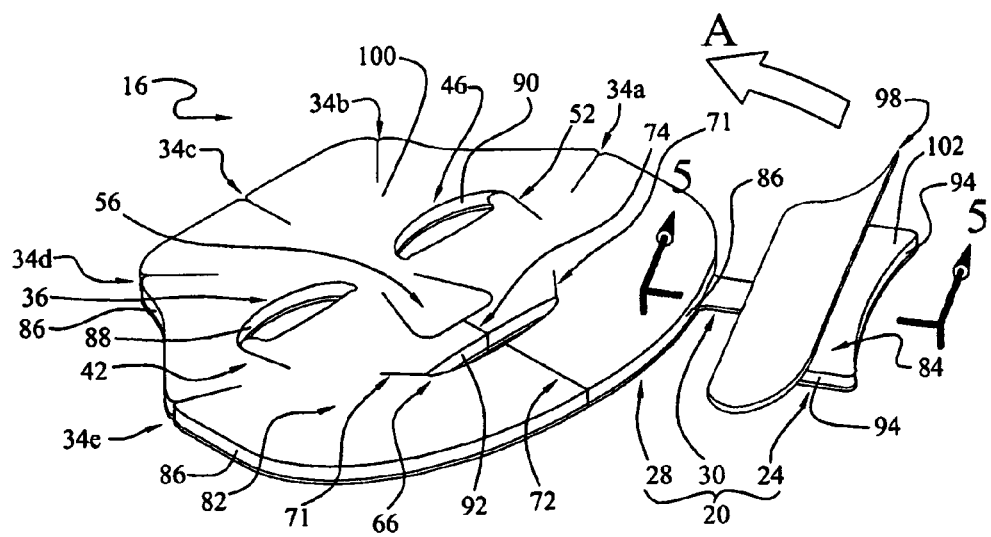
FIG. 3 is a perspective view of the opposite side of the active iontophoresis patch of FIG. 2 freed of the large release liner shown therein, thereby revealing the surface of the iontophoresis patch that is used to engage an intended treatment region on the skin of a subject.

FIG. 3 is a perspective view of the opposite side of iontophoresis patch 16 from that seen in FIG. 2.

In FIG. 3 large release liner 96 has been removed from active electrode segment 82 of adhesive matrix 80. Revealed as a result is an active skin contact surface 100 of active electrode segment 82 of adhesive matrix 80. Active skin contact surface 100 actually engages and releasable secures the portion of iontophoresis patch 16 at active electrode region 28 of substrate 20 to the skin of a subject over an intended treatment region.

As suggested by arrow A in FIG. 3, small release liner 98 is in the process of being peeled from return electrode segment 84 of adhesive matrix 80. Revealed as a result is a return skin contact surface 102 of active electrode segment 82 of adhesive matrix 80. Return skin contact surface 102 actually engages and releasable secures the portion of iontophoresis patch 16 at return electrode region 24 of substrate 20 to the skin of a subject at a location that is distanced from the intended treatment region engaged by active skin contact surface 100 of active electrode segment 82 of adhesive matrix 80.

Figure 4:
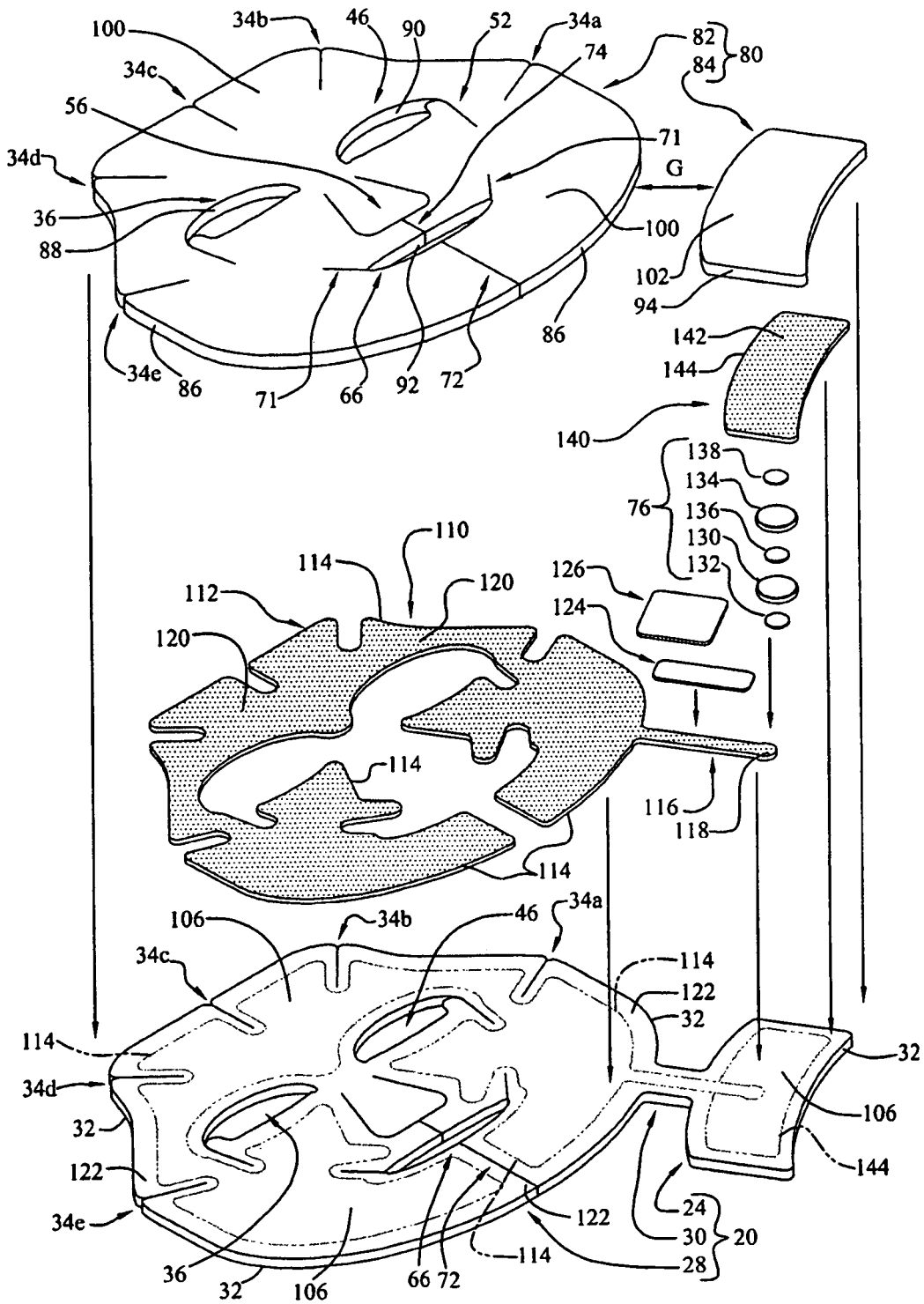
FIG. 4 is an exploded perspective view of the active iontophoresis patch of FIG. 3 showing the therapeutic face of the substrate of the iontophoresis patch, the adhesive matrix by which the iontophoresis patch is secured to the skin of a subject, and elements of the iontophoresis patch that are sandwiched therebetween.

FIG. 4 is an exploded perspective view of iontophoresis patch 16 of FIG. 3. There, both active electrode segment 82 and return electrode segment 84 of adhesive matrix 80 are depicted above and separated from substrate 20, distanced from each other by a gap G that corresponds in size to the extent of bridge portion 30 of substrate 20 between active electrode region 28 and return electrode region 24. Revealed thereby is a therapeutic face 106 of substrate 20 that is configured for disposition toward the skin of subject 10. The portion of therapeutic face 106 located on active electrode region 28 is configured for disposition toward the intending treatment region, while portion of therapeutic face 106 located on return electrode region 24 of substrate 20 is configured for disposition toward the skin of subject 10 at a location that is outside of the intended treatment region.

Sandwiched between active electrode segment 82 of adhesive matrix 80 and therapeutic face 106 of substrate 20 in active electrode region 28 is a flexible, first electrically conductive layer 110. First electrically conductive layer 110 includes an extensive active electrode portion 112 that is possessed of a complexly-shaped periphery 114. First electrically conductive layer 110 also includes a relatively smaller, linear electrical interconnection strip 116 that projects outwardly from periphery 114 of active electrode portion 112 and terminates at the free end thereof in a slightly enlarged, rounded battery contact tip 118. The surface of active electrode portion 112 of first electrically conductive layer 110 visible in FIG. 4, defines a driving face 120 of active electrode portion 112 that becomes located on the side of first electrically conductive layer 110 remote from substrate 20 in the assembled condition of iontophoresis patch 16.

Superimposed by way of reference in phantom on therapeutic face 106 of substrate 20 is an outline of the position assumed by periphery 114 of first electrically conductive layer 110 in the assembled condition of iontophoresis patch 16 shown in FIGS. 2 and 3. Then, active electrode portion 112 of first electrically conductive layer 110 is disposed on the portion of therapeutic face 106 of substrate 20 located on active electrode region 28 thereof. Electrical interconnection strip 116 rests against the side of bridge portion 30 of substrate 20 shown in FIG. 4, extending between active electrode region 28 and return electrode region 24 of substrate 20. Battery contact tip 118 of interconnection strip 116 is disposed relatively centrally on therapeutic face 106 of substrate 20 in return electrode region 24 thereof.

From the phantom depiction of active electrode portion 112 and electrical interconnection strip 116 of first electrically conductive layer 110 it can be appreciated that active electrode portion 112 of first electrically conductive layer 110 is smaller in extent than is active electrode segment 82 of substrate 20. Further, in the assembled condition of iontophoresis patch 16, periphery 114 of active electrode portion 112 of first electrically conductive layer 110 is positioned interior of exterior periphery 32 of substrate 20 in return electrode region 24 thereof. As a result, the portions of therapeutic face 106 immediately adjoining active electrode portion 112 of first electrically conductive layer 110 define a margin 122 of therapeutic face 106 of substrate 20 in active electrode portion 28 that is free of active electrode portion 112.

Margin 122 thus circumscribes active electrode portion 112 of first electrically conductive layer 110 interior of periphery 32 of substrate 20 in of return electrode region 24 thereof, but margin 122 can be larger or smaller, locally or comprehensively, than shown in FIG. 4 without departing from teachings of the present invention. Indeed, locally or comprehensively margin 122 may have no size whatsoever, in which case periphery 114 of active electrode portion 112 of first electrically conductive layer 110 will be coincident with periphery 32 of substrate 20 at selected or at all locations in return electrode region 24 thereof.

In the assembled condition of iontophoresis patch 16, active electrode segment 82 of adhesive matrix 80 is affixed to driving face 120 of first electrically conductive layer 110 and to all or some of any adjacent, exposed margin 122 of therapeutic face 106 of substrate 20 in active electrode region 28 thereof.

With electrical interconnection strip 116 disposed on bridge portion 30 of substrate 20, an electrical insulator strip 124 is applied over all of electrical interconnection strip 116, other than battery contact tip 118 thereof. As thusly enclosed by bridge portion 30 of substrate 20 and electrical insulator strip 124, electrical interconnection strip 116 functions as an insulated conductor electrically coupling battery contact tip 118 thereof with active electrode portion 112 of first electrically conductive layer 110. To enhance the mechanical integrity of this assembled composite structure, a backing patch 126 is applied over electrical insulator strip 124 and the entirety of the surface of bridge portion 30 to either side thereof.

Power source 76 is then assembled on battery contact tip 118 of electrical interconnection strip 116 in electrical connection therewith. As seen by way of example only, power source 76 includes a planar first battery 130 that is adhered to battery contact tip 118 of electrical interconnection strip 116 by an electrically conductive first adhesive dot 132, and a planar second battery 134 that is electrically series-connected with and adhered to first planar battery 130 by an electrically conductive second adhesive dot 136. First adhesive dot 132 thus functions as an electrical connection for power source 76 to first electrically conductive layer 110. An electrically conductive third adhesive dot 138 disposed on the opposite side of second battery 134 from second adhesive dot 136 completes the assembly of power source 76. Third adhesive dot 138 serves to electrically couple that assembly to further elements of iontophoresis patch 16 that are mounted atop power source 76 against therapeutic face 106 of substrate 20 in return electrode region 24 thereof.

Those further elements of iontophoresis patch 16 include a flexible, second electrically conductive layer 140 having a receiving face 142 shown in FIG. 4, and return electrode segment 84 of adhesive matrix 80 that is used to sandwich second electrically conductive layer 140 against power source 76 and return electrode region 24 of substrate 20. Third adhesive dot 138 thus functions as an electrical connection for power source 76 to the face of second electrically conductive layer 140 opposite from receiving face 142. Second electrically conductive layer 140 has a periphery 144 that, for enhanced clarity, is also superimposed in phantom on therapeutic face 106 of substrate 20 in return electrode region 24 thereof. In the assembled condition of iontophoresis patch 16, return electrode segment 84 of adhesive matrix 80 is affixed to return face 144 of second electrically conductive layer 140 and to all or some of any adjacent, exposed portions of therapeutic face 106 of substrate 20 in return electrode region 24 thereof.

Periphery 114 of first electrically conductive layer 110 is so configured relative to active electrode region 28 of substrate 20 as to prevent first electrically conductive layer 110 from occluding actual apertures through the structure of substrate 20, such as right eye aperture 36, left eye aperture 46, and mouth aperture 66. While not required by teachings of the present invention, as shown in FIG. 4, periphery 114 of first electrically conductive layer 110 does not intersect with virtual apertures, such as nose aperture 56 in substrate 20, or with fitting features of substrate 20, such as exterior fitting slits 34a, 34b, 34c, 34d, 34e, interior fitting slits 42, 52, 71, exterior adjustment slit 72, and interior adjustment slit 74.

Figure 5:
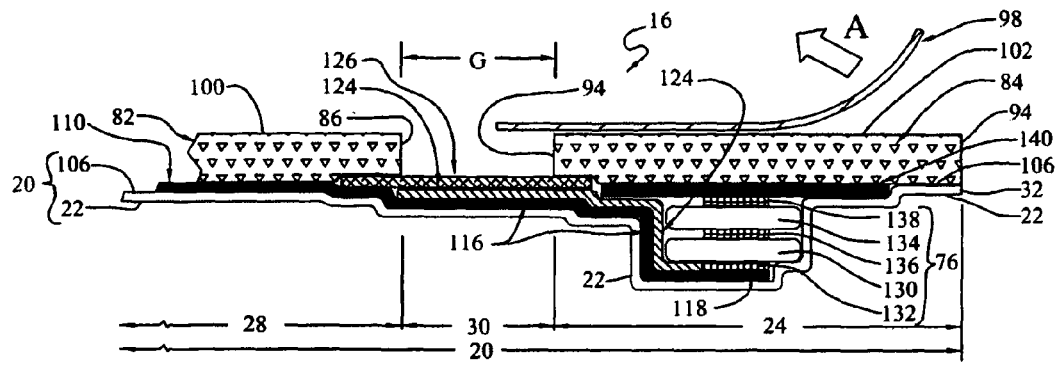
FIG. 5 is a fragmentary cross-sectional elevation view of the active iontophoresis patch of FIG. 3 taken along section line 5-5 shown therein.

FIG. 5 is a cross-sectional elevation view of a portion of iontophoresis patch 16 taken along section line 5-5 in FIG. 3. In FIG. 5, the vertical dimension has been enlarged disproportionately to the horizontal dimension, thereby to enhance the comprehension to be secured therefrom of the interactions of the assembled elements of iontophoresis patch 16 discussed previously. As a result of necessity, while FIG. 5 presents in a single edge view both outer face 22 and therapeutic face 106 of substrate 20, the planar quality of substrate 20 is severely distorted in FIG. 5.

In particular, bridge portion 30 of substrate 20, which interconnects return electrode region 24 and active electrode region 28 of substrate 20, carries directly on therapeutic face 106 of substrate 20 electrical interconnection strip 116 of first electrically conductive layer 110.

Sandwiched between electrical interconnection strip 116 and second electrically conductive layer 140 are the assembled elements of power source 76. Second electrically conductive layer 140 directly electrically engages a side of third adhesive dot 138, while the opposite side of third adhesive dot 138 directly electrically engages one of the flat faces of second battery 134. The opposite face of second battery 134 directly electrically engages a side of second adhesive dot 136, while the opposite side of second adhesive dot 136 directly electrically engages one of the flat faces of first battery 130. The opposite face of first battery 130 directly electrically engages a side of first adhesive dot 132. Battery contact tip 118 at the terminus of electrical interconnection strip 116 directly electrically engages the opposite side of first adhesive dot 132.

One end of electrical insulator strip 124 is interposed between electrical interconnection strip 116 and the other elements of power source 76. The other end of electrical insulator strip 124 covers the balance of the length of electrical interconnection strip 116 to active electrode portion 112 of first electrically conductive layer 110. Backing patch 126 in turn covers electrical insulator strip 124, structurally reinforcing bridge portion 30 of substrate 20 and bridging gap G between active electrode segment 82 and return electrode segment 84 of adhesive matrix 80.

As suggested by arrow A in FIG. 5, small release liner 98 is in the process of being peeled from return skin contact surface 102 of return electrode segment 84 of adhesive matrix 80. This will eventually free return skin contact surface 102 of return electrode segment 84 for the releasable attachment of return electrode region 24 of substrate 20 to the skin of a subject. Consistent with FIG. 3, in FIG. 5 large release liner 96 no longer covers active skin contact surface 100 of active electrode segment 82 of adhesive matrix 80. Thus, active skin contact surface 100 is ready to effect the releasable attachment of active electrode region 28 of substrate 20 to the skin of a patient.

Figure 6A:
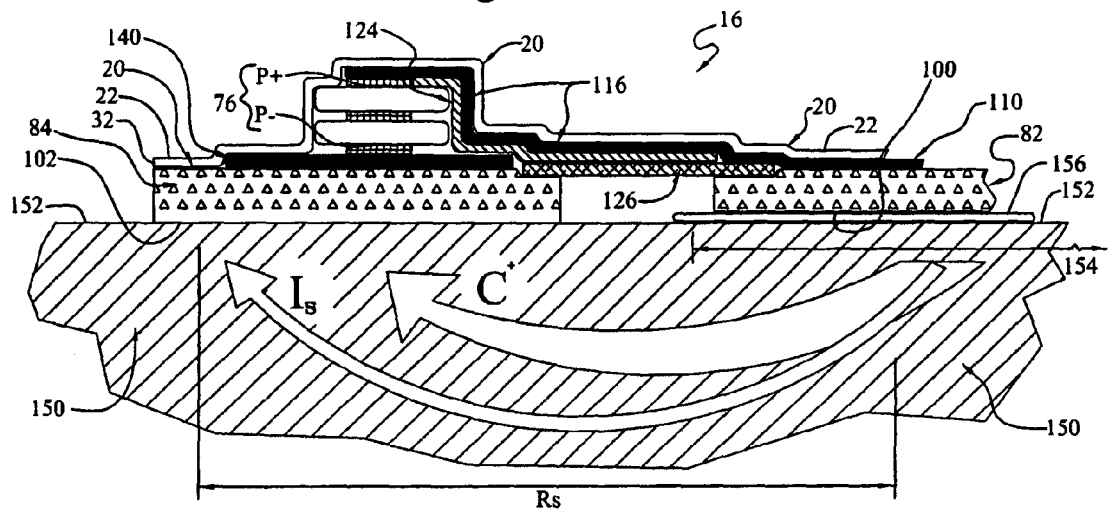
FIG. 6A is diagrammatic cross-sectional elevation view of the active iontophoresis patch of FIG. 5 inverted and disposed against the skin of a subject, thereby to illustrate the movement of a cosmetic agent of positive polarity through skin of the subject.
Figure 6B:
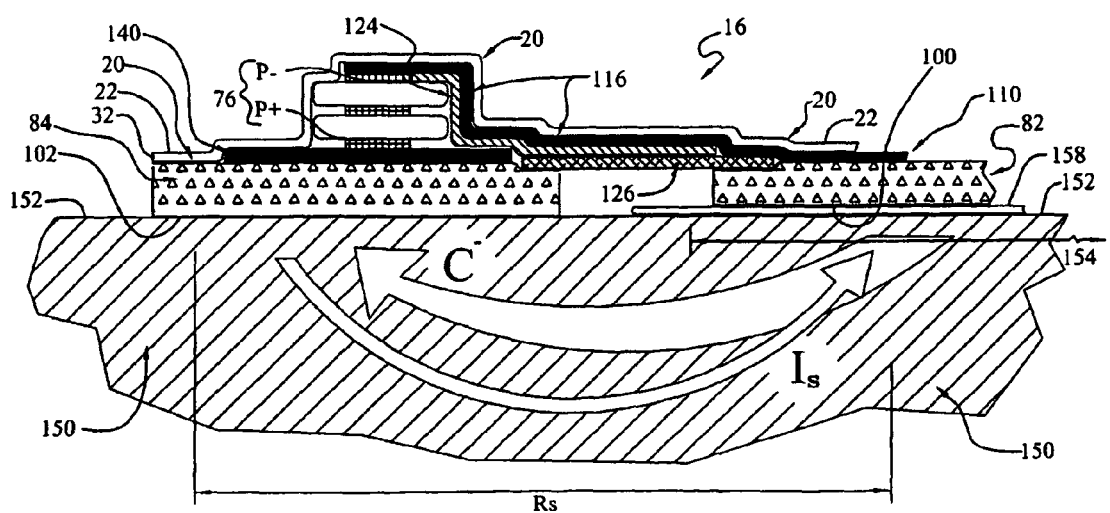
FIG. 6B is a diagram like that of FIG. 6A illustrating the movement of a cosmetic agent of negative polarity through skin of a subject.

FIGS. 6A and 6B are related diagrams that compare the movement of cosmetic agents of differing polarities through the skin 150 of a user of iontophoresis patch 16.

FIG. 6A illustrates the movement of molecules of a positive cosmetic agent $C^+$ that exhibits a net positive polarity To use iontophoresis patch 16, the surface 152 of skin 150 within a treatment region 154 is first coated with a cosmeceutical solution 156 that contains cosmetic agent $C^+$. Therapeutic face 106 of substrate 20 is oriented toward the skin 150, and iontophoresis patch 16 is disposed against surface 152 thereof. Active skin contact surface 100 of active electrode segment 82 of adhesive matrix 80 engages surface 152 of skin 150 through cosmeceutical solution 156, and return skin contact surface 102 of return electrode segment 84 of adhesive matrix 80 engages surface 152 of skin 150 outside of treatment region 154. Due to the properties of the material of adhesive matrix 80 discussed earlier, iontophoresis patch 16 becomes secured to skin 150, but in such a manner that both active electrode segment 82 and return electrode segment 84 of adhesive matrix 80 can be removed from, stored, and reapplied to surface 154 repeatedly without incurring damage to iontophoresis patch 16.

Then as shown in FIG. 6A, active electrode segment 82 and return electrode segment 84 of adhesive matrix 80 each electrically conductively engage surface 152 of skin 150 at separated locations. Aside from the conductivity of skin 150, these locations are electrically isolated from each other. The positive pole P+ of power source 76 is coupled directly or indirectly through active electrode segment 82 of adhesive matrix 80 to skin 150. The negative pole P− of power source 76 is coupled directly or indirectly through return electrode segment 84 of adhesive matrix 80 to skin 150 at a location that is remote from active electrode segment 82. The electromotive differential thusly applied to skin 150 between active electrode segment 82 and return electrode segment 84 induces molecules of cosmetic agent C+ to move as positive ions out of cosmeceutical solution 156 toward skin 150, across unbroken surface 152 of skin 150, and through skin 150 in the direction of return electrode segment 84 of adhesive matrix 80. This movement is indicated in FIG. 6A by an arrow labeled C+.

In electrical circuits, the flow of electrical current is conventionally indicated as a flow through the circuit from the positive to the negative pole of the power source employed therewith. Therefore, in FIG. 6A, an electrical skin current $I_S$ is schematically indicated by a solid arrow to flow through skin 150 from active electrode segment 82 of adhesive matrix 80, which is associated with positive pole P+ of power source 76, to return electrode segment 84 of adhesive matrix 80, which is associated with the negative pole P− of power source 76. In the use of iontophoresis patch 16 to administer a positive cosmetic agent C+, the direction of movement of molecules of cosmetic agent C+ through skin 150 thus coincides with the direction of skin current $I_S$.

While living tissue is a conductor of electric current, living tissue does nonetheless resist the flow of electrical current therethrough. It is the function of power source 76 to apply a sufficient electromotive force differential through skin 150 between active electrode segment 82 and return electrode segment 84 of adhesive matrix 80 as to overcome this resistance. The presence of electrical resistance in skin 112 is indicated schematically in FIG. 5A as skin resistance $R_S$.

Skin resistance $R_S$ varies among human subjects over a wide range. At the commencement of the passage of a skin current through the skin, the resistance of the skin to the passage of electrical current is far higher than is skin resistance $R_S$ once a flow of current has been established. Nonetheless, within a few minutes of beginning to conduct a skin current, skin resistance $R_S$ of most subjects undergoes transient changes and stabilizes at about 10 kilo-ohms, or more broadly stabilizes in a range of from about 10 kilo-ohms to about 50 kilo-ohms.

In FIG. 6B, the transcutaneous administration is depicted of molecules of a negative cosmetic agent C− that exhibits a net negative polarity.

Surface 152 of skin 150 within treatment region 154 is coated with a cosmeceutical solution 158 that contains cosmetic agent C−. Therapeutic face 106 of substrate 20 is oriented toward skin 150, and iontophoresis patch 16 disposed against surface 152 thereof. Active electrode segment 82 and return electrode segment 84 of adhesive matrix 80 each electrically conductively engage surface 152 of skin 150 at separated locations. Aside from the conductivity of skin 150, these locations are electrically isolated from each other. The presence of electrical resistance in skin 150 is indicated schematically in FIG. 6B as skin resistance $R_S$.

To infuse cosmetic agent C−, the electrical components of a medicament patch incorporating teachings of the present invention must be altered from those described above relative to FIG. 6A. Accordingly, negative pole P− of power source 76 is coupled directly or indirectly through active electrode segment 82 of adhesive matrix 80 to skin 150. The positive pole P+ of power source 76 is coupled directly or indirectly through return electrode segment 84 of adhesive matrix 80 to skin 150 at a location that is remote from active electrode segment 82. The electromotive differential thusly applied to skin 150 between active electrode segment 82 and return electrode segment 84 induces molecules of cosmetic agent C− to move as negative ions out of cosmeceutical solution 158 toward skin 150, across unbroken surface 152 of skin 150, and through skin 150 in the direction of return electrode segment 84 of adhesive matrix 80. This movement is indicated in FIG. 6B by an arrow labeled C−.

Recalling that the flow of electrical current in an electrical circuit is conventionally indicated as a flow through the circuit from the positive to the negative pole of the power source employed therewith, in FIG. 6B, a skin current $I_S$ schematically indicated by a solid arrow to flow through skin 150 toward active electrode segment 82 of adhesive matrix 80, which is associated with negative pole P− of power source 76, from return electrode segment 84 of adhesive matrix 80, which is associated with positive pole P+ of power source 76. In the use of iontophoresis patch 16 to administer cosmetic agent C−, the movement of molecules of a negative cosmetic agent C− through skin 150 is in a direction that is opposite to that of skin current $I_S$.

According to another aspect of the present invention, a cosmetic treatment system employing an active iontophoresis patch, such as iontophoresis patch 16 in FIGS. 1-5, is driven by a power source that, in contrast to power source 76, is not carried on that patch itself. Such an external power source can be driven by disposable or rechargeable batteries, or by current obtained from an electrical wall socket. The active electrode region and the return electrode region of the substrate of the iontophoresis patch each include a respective electrical contact that enables cables from individual poles of the external power source to effect an electrical coupling of those respective poles to separated locations on the skin through, respectively, the active electrode portion and the return electrode portion of the adhesive matrix employed with the iontophoresis patch. An external power source permits the rapid delivery a cosmetic agent into the skin as compared, for example, with the rate of delivery that is typically available using a power source of a size sufficiently small as to permit it to be carried on the iontophoresis patch itself.

Figure 7:
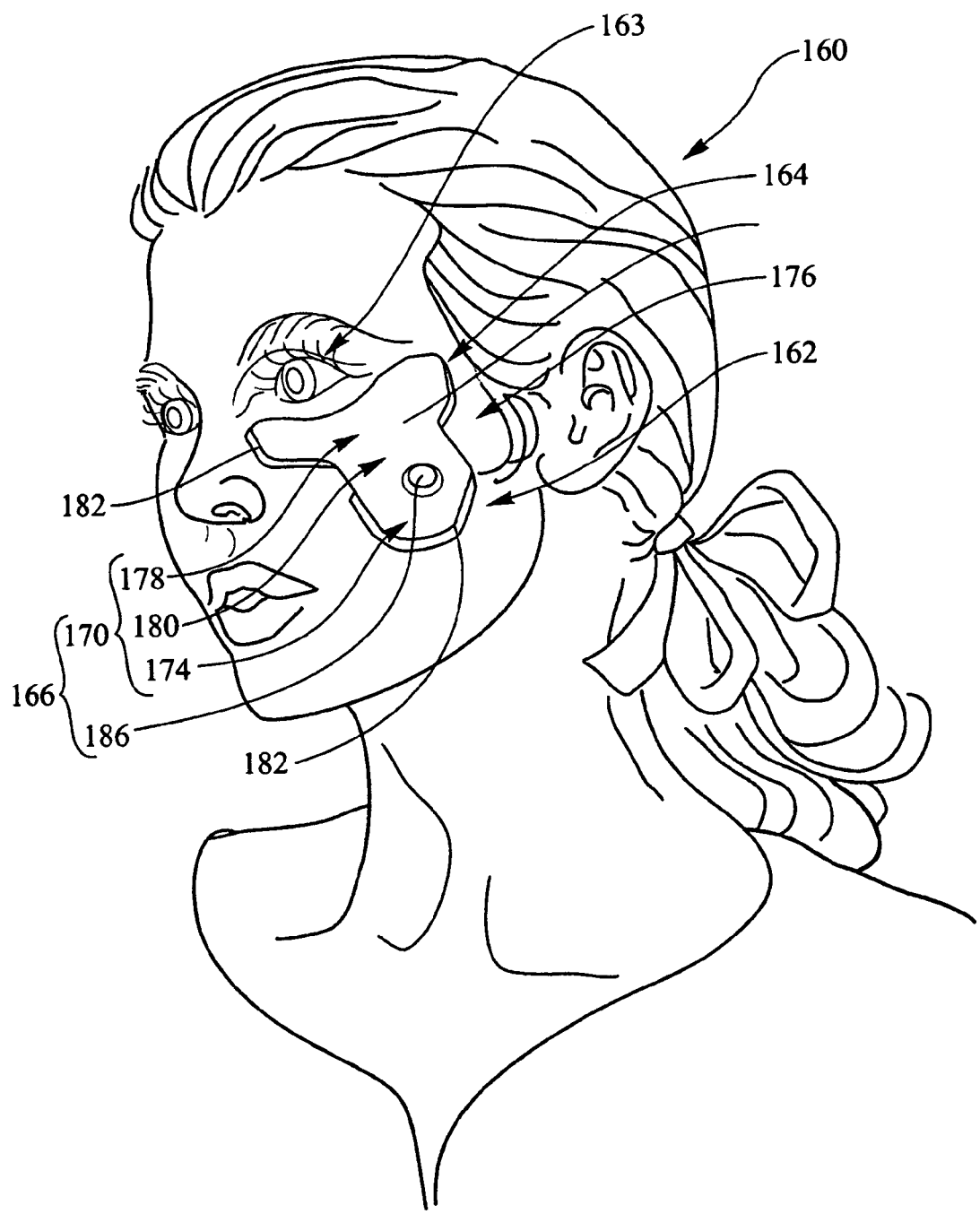
FIG. 7 is a perspective view of a second embodiment of an active iontophoresis patch incorporating teachings of the present invention being worn by a subject during the administration of a cosmetic agent to the skin of the lower lid of the left eye thereof.

FIG. 7 depicts another subject 160 during the administration of a cosmetic agent to the skin of a specific portion of the face 162 thereof. Toward that end, subject 160 is wearing over the lower lid of the left eye 163 a second embodiment of an active iontophoresis cosmetic agent administration system 164 that incorporates teachings of the present invention. While so doing, subject 160 is nonetheless able to engage in activity, because administration system 164 is entirely self-contained, and is not supplied with power from any external power source.

Administration system 164 takes the form of a fully-integrated, active iontophoresis patch 166 that is secured to the skin in an intended treatment region on the lower lid of left eye 163 of subject 160 for the duration of a predetermined treatment period. The length of the treatment period during which iontophoresis patch 166 must be worn is determined by the rate at which iontophoresis patch 166 delivers a cosmetic agent through the skin of subject 160 and the total dose of the cosmetic agent that is to be administered. The cosmetic agent is contained in a cosmeceutical solution that is applied as a coating to the skin of the intended treatment region before iontophoresis patch 166 is secured thereto.

According to one aspect of the present invention, iontophoresis patch 166 is so constructed as to be repeatedly releasable securable to the skin of subject 160. Thus, iontophoresis patch 166 can be repositioned on the skin of subject 160 as needed, or iontophoresis patch 166 can be removed at the end of the predetermined treatment period, washed, and stored until required for a subsequent treatment session involving subject 160. Once the treatment region has again been coated with a cosmeceutical solution containing the same, or even a different, cosmetic agent, iontophoresis patch 166 is again releasably secured to the skin of the intended treatment region for a second predetermined treatment period.

While it is not necessary according to teachings of the present invention that such steps be repeatable indefinitely, it is contemplated using the materials and the constructions disclosed hereinafter that a cosmetic iontophoresis patch, such as iontophoresis patch 166, be reusable at least on a plurality of occasions, possibly in a range of from 2 to 15 occasions, and more narrowly in a range of from 5 to 10 occasions.

Iontophoresis patch 166 is a comparatively thin structure having a layered construction that will be explored in detail subsequently. Nonetheless, it can be noted here that iontophoresis patch 166 includes an irregularly-shaped, flexible biocompatible substrate 170 having an outer face 172 that forms the surface of iontophoresis patch 166 visible in FIG. 7. Substrate 170 is substantially coextensive with the maximum extent of iontophoresis patch 166 and thus serves as a unifying structure for the balance of the elements of iontophoresis patch 166.

When not secured in conformance to the skin of subject 160 during use, iontophoresis patch 166 is capable of disposition for storage in an entirely flat, planar configuration, or of being curled back upon itself into a roll. While susceptible to folding, sharp bending of iontophoresis patch 166 is not recommended, as doing so is likely over time to degrade the layered construction thereof and, consequently, to reduce the number of occasions on which iontophoresis patch 166 can reliably be put to use.

Substrate 170 includes a return electrode region 174 that is shown in FIG. 7 to be releasable secured to the cheek 176 of subject 160 at a distance from the intended treatment region to which a cosmetic agent is intended to be transcutaneously administered. Substrate 170 also includes an active electrode region 178 that is separated from return electrode region 174 by a bridge portion 180 of substrate 170. Active electrode region 178 of substrate 170 is shaped to enable iontophoresis patch 166 to closely conform to the skin of subject 160 over an intended treatment region as irregular as the lower lid of the left eye 163. Thus, substrate 170 has an exterior periphery 182 in active electrode region 178 that is particularly shaped to facilitate the conformance of substrate 170 to the skin of the subject 160 over the intended treatment region.

A power source 186 is carried on return electrode region 174 interior of exterior periphery 188 of substrate 170 in return electrode region 174 thereof. Power source 186 is electrically coupled with elements of iontophoresis patch 166 not visible in FIG. 7 so as to cause a cosmetic agent in a cosmeceutical solution on the skin of subject 160 beneath active electrode region 178 of substrate 170 to migrate away from iontophoresis patch 166 into the skin of subject 160.

For most cosmetic applications, the output voltage produced by a power source, such as power source 186, ranges from about 1.00 volt to about 15.00 volts. Alternatively, the output voltage produced by power source 186 ranges from about 2.00 volts to about 9.00 volts, or from about 3.00 volts to about 6.00 volts. Power source 186 is, by way of example, capable of delivering direct current at about 3 volts potential. Power source 186 may be a single battery of higher or lower output potential, or power source 186 may be a plurality of series-connected batteries of equal or unequal output potential.

In general, the greater the output voltage produced by a mobile power source, such as power source 186 associated with an active cosmetic transdermal patch, the larger will be the skin current $I_S$ produced by that patch, and the shorter will be the treatment period required to enable that patch to administer any predetermined total amount of cosmetic agent. While such a result is salutary relative to minimizing the time during which a subject is required to be encumbered by wearing the patch, the larger the skin current $I_S$ produced by a patch, the greater the likelihood that a wearer of the patch will experience uncomfortable sensations, or even pain, during treatment. Accordingly, an unavoidable tradeoff exists between the desirable ends of comfort and of speedy treatment. Lower levels of power source output are calculated to increase subject comfort and to improve the likelihood that a subject will be willing to successfully complete a prescribed course of treatment, once that course of treatment has been undertaken.

Figure 8:
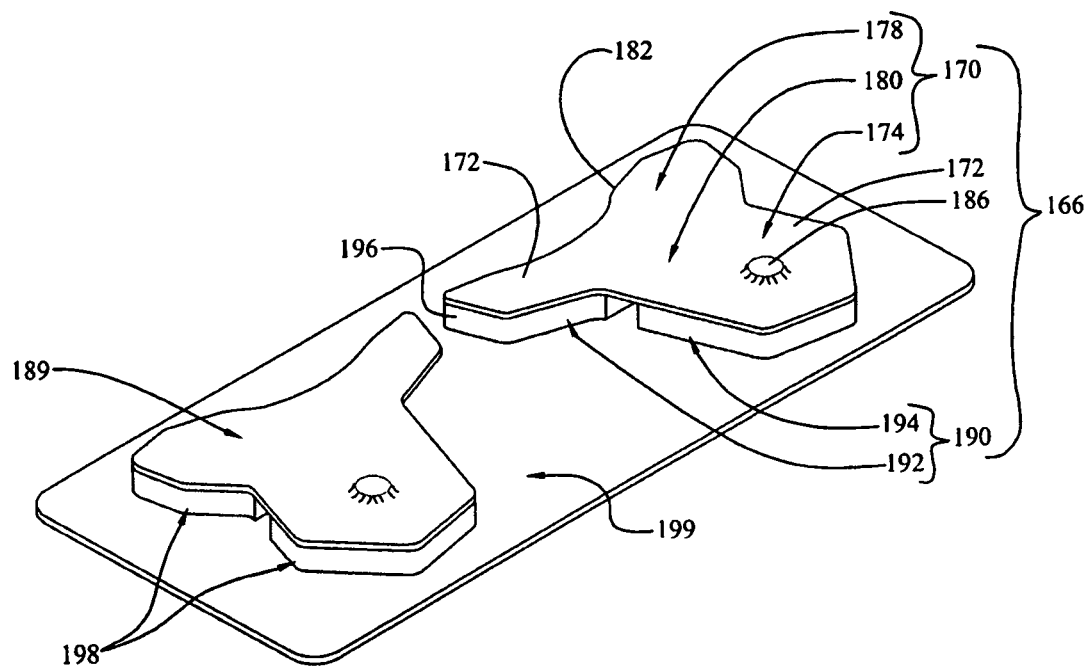
FIG. 8 is a perspective view in planar disposition of a matched pair of active iontophoresis patches of the type shown in FIG. 7 carried together on a unitary release liner.

FIG. 8 includes a perspective view of iontophoresis patch 166 of FIG. 7, as well as a perspective view of a mirror-image iontophoresis patch 189 that suited for use on the lower lid of the right eye of subject 160. Both of iontophoresis patches 166, 189, are shown in the planar in which iontophoresis patches 166, 189, are marketed and commonly stored between uses. The layered structure of iontophoresis patches 166, 189, will be more fully appreciated by focusing on the details of iontophoresis patch 166 alone.

Substrate 170 is depicted as an outer skin for a relatively thicker, electrically conductive, adhesive matrix 190. Adhesive matrix 190 is affixed to the side of substrate 170 opposite from outer face 172 thereof. Adhesive matrix 190 includes an active electrode segment 192 that is carried on active electrode region 178 of substrate 170 and a return electrode segment 194 that is carried on return electrode region 174 of substrate 170. No portion of adhesive matrix 190 is affixed to bridge portion 180 of substrate 170. As a result, active electrode portion 172 of adhesive matrix 190 is electrically isolated from return electrode region 174 of adhesive matrix 190 in the plane of adhesive matrix 190.

An exterior side edge surface 196 of active electrode segment 192 of adhesive matrix 190 coincides with exterior periphery 182 of substrate 170 in active electrode region 178 thereof. One face of adhesive matrix 190 is permanently secured to substrate 170, but the opposite, exposed face of adhesive matrix 190 is capable of being repeatedly secured to and removed from the skin of subject 160. Thus, it is adhesive matrix 190 that actually retains iontophoresis patch 166 on the lower lid of left eye 163 of subject 160 in FIG. 7.

When not in use, the exposed face of adhesive matrix 190 and the exposed face of a mirror-image adhesive matrix 198 of iontophoresis patch 189 are protected by a comprehensive release liner 199 from which each of iontophoresis patches 166, 189, can be independently, selectively, and repeatedly removed. Release liner 199 facilitates the handling and storage of iontophoresis patches 166, 189. Alternatively, each of iontophoresis patches 166, 189, can so protected by individual release liners, or each of active electrode segment 192 and return electrode segment 194 of adhesive matrix 190 and the similar components of iontophoresis patch 189 can be so protected by respective smaller individual release liners. All such release liners also function to maintain return electrode segment 194 of adhesive matrix 190 and the corresponding component of iontophoresis patch 189 in electrical isolation, until such time as the energy of power source 186 or the corresponding component of iontophoresis patch 189 is actually needed.

Figure 9:
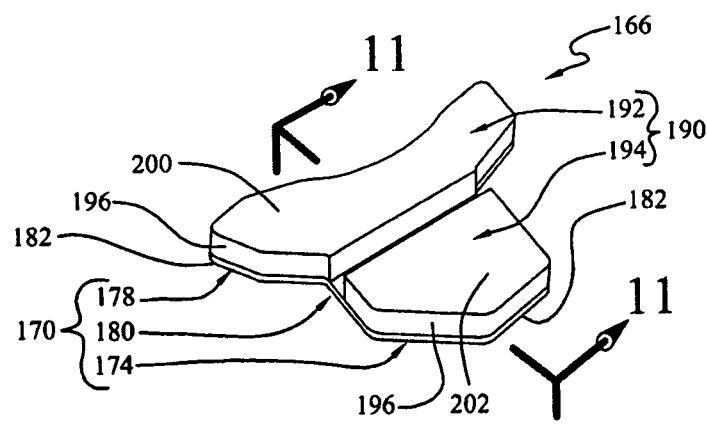
FIG. 9 is a perspective view of the opposite side of the active iontophoresis patch appearing on the right side of FIG. 8 freed of the unitary release liner shown therein, thereby revealing the surface of the iontophoresis patch that is used to engage the skin of a subject.

In FIG. 9, iontophoresis patch 166 has been removed from release liner 199 and turned over, thereby affording a perspective view of the opposite side of iontophoresis patch 166 from that seen in FIG. 8.

Revealed as a result is an active skin contact surface 200 of active electrode segment 192 of adhesive matrix 190. Active skin contact surface 200 actually engages and releasable secures the portion of iontophoresis patch 166 at active electrode region 178 of substrate 170 to the skin of a subject over an intended treatment region. Also revealed is a return skin contact surface 202 of active electrode segment 192 of adhesive matrix 190. Return skin contact surface 202 actually engages and releasable secures the portion of iontophoresis patch 166 at return electrode region 174 of substrate 170 to the skin of a subject at a location that is distanced from the intended treatment region engaged by active skin contact surface 200 of active electrode segment 192.

Figure 10:
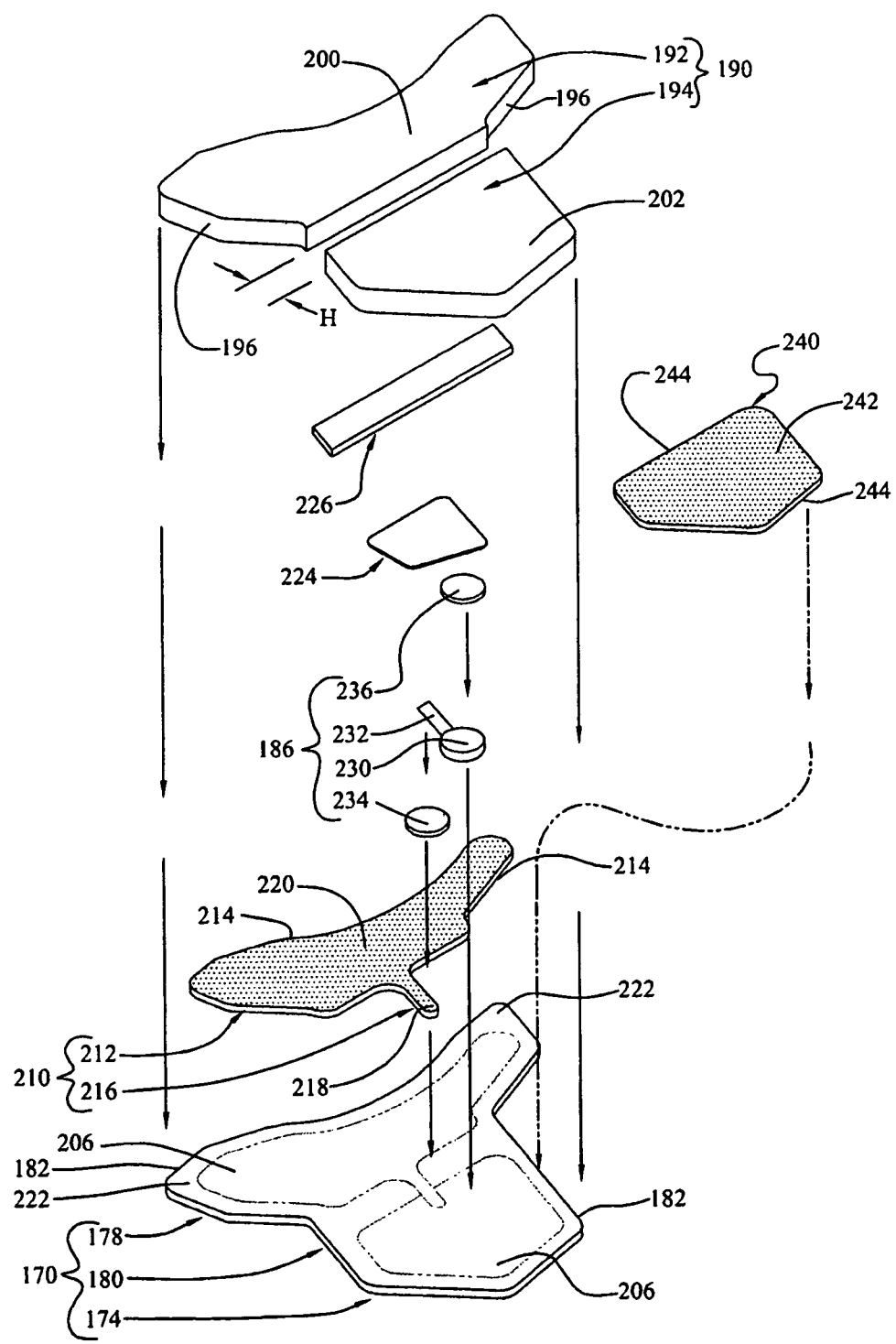
FIG. 10 is an exploded perspective view of the active iontophoresis patch of FIG. 9 showing the therapeutic face of the substrate of the iontophoresis patch, the adhesive matrix by which the iontophoresis patch is secured to the skin of a subject, and elements of the iontophoresis patch that are sandwiched therebetween.

FIG. 10 is an exploded perspective view of iontophoresis patch 166 of FIG. 9. There, both active electrode segment 192 and return electrode segment 194 of adhesive matrix 190 are depicted above and separated from substrate 170, distanced from each other by a gap H that corresponds in size to the extent of bridge portion 180 of substrate 170 between active electrode region 178 and return electrode region 174. Revealed thereby is a therapeutic face 206 of substrate 170 that is configured for disposition toward the skin of subject 160. The portion of therapeutic face 206 located on active electrode region 178 is configured for disposition toward the intended treatment region, while the portion of therapeutic face 206 located on return electrode region 174 of substrate 170 is configured for disposition toward the skin of subject 160 at a location that is outside of the intended treatment region.

Sandwiched between active electrode segment 192 of adhesive matrix 190 and therapeutic face 206 of substrate 170 in active electrode region 178 thereof is a flexible, first electrically conductive layer 210. First electrically conductive layer 210 includes an active electrode portion 212 that is possessed of an irregularly-shaped periphery 214. First electrically conductive layer 210 also includes a relatively smaller, linear electrical interconnection strip 216 that projects outwardly from periphery 214 of active electrode portion 212 and terminates at the free end thereof in a battery contact tip 218. The surface of active electrode portion 212 of first electrically conductive layer 210 visible in FIG. 10, defines a driving face 220 of active electrode portion 212 that becomes located on the side of first electrically conductive layer 210 remote from substrate 170 in the assembled condition of iontophoresis patch 166.

Superimposed by way of reference in phantom on therapeutic face 206 of substrate 170 is an outline of the position assumed by periphery 214 of first electrically conductive layer 210 in the assembled condition of iontophoresis patch 166 shown in FIGS. 8 and 9. There, active electrode portion 212 of first electrically conductive layer 210 is disposed on the portion of therapeutic face 206 of substrate 170 located on active electrode region 178 thereof. Electrical interconnection strip 216 rests against the side of bridge portion 180 of substrate 170 shown in FIG. 10, extending between active electrode region 178 and return electrode region 174. Battery contact tip 218 of electrical interconnection strip 216 is disposed relatively centrally on therapeutic face 206 of substrate 170 in return electrode region 174 thereof.

From the phantom depiction of active electrode portion 212 and electrical interconnection strip 216 of first electrically conductive layer 210 it can be appreciated that active electrode portion 212 of first electrically conductive layer 210 is smaller in extent than is active electrode region 178 of substrate 170. Further, in the assembled condition of iontophoresis patch 166, periphery 214 of active electrode portion 212 of first electrically conductive layer 210 is positioned interior of exterior periphery 182 of substrate 170 in return electrode region 174 thereof. As a result, the portions of therapeutic face 206 immediately adjoining active electrode portion 212 of first electrically conductive layer 208 define a margin 222 of therapeutic face 206 of substrate 170 in active electrode portion 172 thereof that is free of active electrode portion 212.

Margin 222 thus circumscribes active electrode portion 212 of first electrically conductive layer 210 interior of periphery 182 of substrate 170 in return electrode region 174 thereof, but margin 122 can be larger or smaller, locally or comprehensively, than shown in FIG. 10 without departing from teachings of the present invention. Indeed, locally or comprehensively margin 222 may have no size whatsoever, in which case periphery 214 of active electrode portion 212 of first electrically conductive layer 210 will be coincident with periphery 182 of substrate 170 in return electrode region 174 at selected or at all locations in return electrode region 174.

In the assembled condition of iontophoresis patch 166, active electrode segment 192 of adhesive matrix 190 is affixed to driving face 220 of first electrically conductive layer 210 and to all or some of any adjacent, exposed margin 222 of therapeutic face 206 of substrate 170 in active electrode region 178.

With electrical interconnection strip 216 disposed on bridge portion 180 of substrate 170, an electrical insulator patch 224 is applied over all of electrical interconnection strip 216, other than battery contact tip 218 thereof. As thusly enclosed by bridge portion 180 of substrate 170 and electrical insulator patch 224, electrical interconnection strip 216 functions as an insulated conductor electrically coupling battery contact tip 118 thereof with active electrode portion 212 of first electrically conductive layer 210. To enhance the mechanical integrity of this assembled composite structure, a backing strip 226 is applied over electrical insulator patch 224 and some or the entire surface of bridge portion 180 to either side thereof.

Power source 186 is then assembled on battery contact tip 218 of electrical interconnection strip 216 in electrical connection therewith. As seen by way of example only, power source 186 includes a single planar battery 230. Battery 230 is provided with an electrically conductive lead 232 that extend radically outwardly from battery 230 in the plane thereof. Lead 232 is adhered to battery contact tip 218 of electrical interconnection strip 216 by an electrically conductive first adhesive dot 234. Thus first adhesive dot 234 functions as an electrical contact for power source 186 to active electrode portion 212. An electrically conductive second adhesive dot 236 disposed on the opposite side of battery 230 from lead 232 and first adhesive dot 234 completes the assembly of power source 186. Second adhesive dot 236 serves to electrically couple that assembly to further elements of iontophoresis patch 166 that are mounted atop power source 186 against electrical contact face 208 of therapeutic face 206 of substrate 170 in return electrode region 174 thereof.

Those further elements of iontophoresis patch 166 include a flexible, second electrically conductive layer 240 having a receiving face 242 shown in FIG. 10, and return electrode segment 194 of adhesive matrix 190 that is used to sandwich second electrically conductive layer 240 against power source 186 and return electrode segment 194 of substrate 170. Second adhesive dot 236 thus functions as an electrical connection for power source 186 to the face of second electrically conductive layer 240 opposite from receiving face 242 thereof. Second electrically conductive layer 240 has a periphery 244 that for enhanced clarity is also superimposed in phantom on therapeutic face 206 of substrate 170 in return electrode region 174 thereof. In the assembled condition of iontophoresis patch 166, return electrode segment 194 of adhesive matrix 190 is affixed to receiving face 242 of second electrically conductive layer 240 and to all or some of any adjacent, exposed portions of therapeutic face 206 of substrate 170 in return electrode region 174 thereof.

Figure 11:
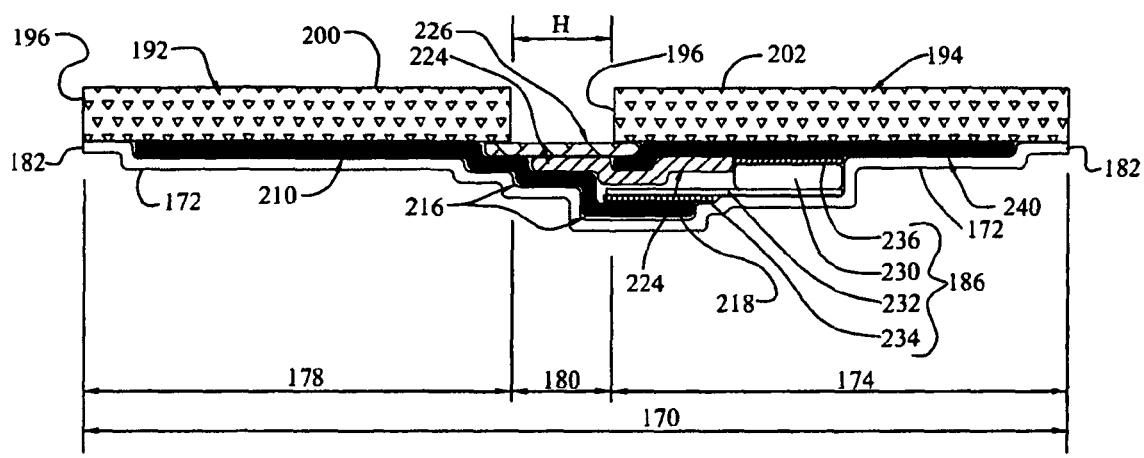
FIG. 11 is a cross-sectional elevation view of the active iontophoresis patch of FIG. 9 taken along section line 11-11 shown therein.

FIG. 11 is a cross-sectional elevation view of iontophoresis patch 166 taken along section line 11-11 in FIG. 9. In FIG. 11, the vertical dimension has been enlarged disproportionately to the horizontal dimension, thereby to enhance the comprehension to be secured therefrom of the interactions of the assembled elements of iontophoresis patch 166 discussed previously. As a result of necessity, while FIG. 11 presents in a single edge view both outer face 172 and therapeutic face 206 of substrate 170, the planar quality of substrate 170 is severely distorted in FIG. 11.

In particular, bridge portion 180 of substrate 170, which interconnects return electrode region 174 and active electrode region 178 of substrate 170, carries directly on therapeutic face 206 of substrate 170 electrical interconnection strip 216 of first electrically conductive layer 210.

Sandwiched between electrical interconnection strip 216 and second electrically conductive layer 240 are the assembled elements of power source 186. Second electrically conductive layer 240 directly electrically engages a side of second adhesive dot 236, while the opposite side of second adhesive dot 236 directly electrically engages one of the flat faces of battery 230. The opposite face of battery 230 is directly electrically engaged by one end of lead 232. The other end of lead 232 makes electrical contact with a side of first adhesive dot 234. Battery contact tip 218 at the terminus of electrical interconnection strip 216 directly electrically engages the opposite side of first adhesive dot 234.

One end of electrical insulator patch 224 abuts a side of second adhesive dot 236 and is interposed between electrical interconnection strip 216 and the other elements of power source 186. The other end of electrical insulator patch 224 covers the balance of the length of electrical interconnection strip 216 to active electrode portion 212 of first electrically conductive layer 210. Backing strip 226 in turn covers electrical insulator patch 224, structurally reinforcing bridge portion 180 of substrate 170 and bridging gap H between active electrode segment 192 and return electrode segment 194 of adhesive matrix 190.

Release liner 199 from FIG. 8 no longer covers either active skin contact surface 200 of active electrode segment 192 of adhesive matrix 80 or return skin contact surface 202 of return electrode segment 194 of adhesive matrix 80. Therefore, active skin contact surface 200 and return skin contact surface 202 are ready to effect the releasable attachment of iontophoresis patch 166 to the skin of a patient.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within the scope thereof.

What is claimed is:

1. A cosmetic iontophoretic face mask for driving a cosmetic agent into skin of a patient's face located adjacent to the face mask, the cosmetic ionotophoretic face mask comprising:

(a) an active electrode including
 a flexible biocompatible substrate having a therapeutic face configured for disposition toward the skin of the patient's face,
 an exterior periphery shaped to facilitate conformance of said substrate to said patient's skin over an intended treatment region,
 a flexible conductive layer disposed on said therapeutic face,
 a driving face located on a distal side of said conductive layer opposite from said substrate and opposite from the patient's skin when said mask is in use,
 an electrically conductive adhesive matrix affixed to said driving face, said electrically conductive matrix being capable of repeatedly releasably securing said active electrode to said patient's skin,
 a cosmetic agent disposed on said substrate to be driving into said patient's skin by iontophoresis, said cosmetic agent having ionic properties so that it may be migrated into the patient's skin by iontophoresis,
 a release liner located on said substrate,
 at least one aperture formed through said substrate, said aperture being defined by a continuous interior periphery of said substrate, said interior periphery that defines said aperture being shaped to facilitate the conformance of said therapeutic face of said substrate to the patient's face,
(b) a return electrode for completing an electrical circuit with said active electrode, said patient's skin and said conductive layer of said face mask,
(c) a release liner adjacent said return electrode,
(d) a power source for electrically powering said face mask to iontophoretically deliver said cosmetic agent from said adhesive matrix to said patient's skin by use of
 an electromotive force through electrical connection and power of said active electrode, said return electrode and said conductive layer,
(e) an active skin contact surface of active electrode that actually engages and releasable secures a portion of iontophoresis patch at active electrode region of said substrate to the skin of a patient, and
(f) a plurality of adhesive dots on said substrate, said dots being electrically connected to said power source;
wherein powering said circuit with said power supply causes the—administration of said cosmetic agent to said patient's face by transcutaneous delivery through the mechanism of iontophoresis;
wherein said exterior periphery of said substrate is provided with an exterior fitting slit formed through said substrate and extending from the exterior periphery thereof into said substrate to permit portions of said substrate adjacent to and on opposite sides of said exterior fitting slit to be overlapped, thereby enhancing conformity of said mask to the patient's face;

wherein said power supply has an output voltage that ranges from about 1.00 volt to about 15.00 volts;

wherein said electrically conductive layer is sandwiched between said active electrode and said therapeutic face of said substrate; and wherein said electrically conductive layer is positioned interior of said exterior periphery of said substrate.

2. The device as recited in claim 1 wherein said cosmetic agent has a capability selected from the group comprising (i) the ability to enhance vitality of the patient's skin, (ii) the ability to enhance vitality of the patient's skin, (iii) the ability to effect a cosmetic undertaking on the patient's skin.

3. The device as recited in claim 1 wherein said cosmetic agent reduces skin sensation through use of a numbing compound in order to prepare said skin for an aggressive cosmetic procedure selected from the group consisting of (i) surface abrasion, (ii) hair removal, and (iii) tattoo erasure.

4. The device as recited in claim 1 wherein during said iontophoresis process, direct electrical current is used to cause ions of said cosmetic agent to cross the surface of said patient's skin and to diffuse into underlying tissue without breaking the surface of said skin.

5. The device as recited in claim 1 further comprising contrasting galvanic materials that when coupled by a fluid medium produce minute electrical currents to power said iontophoresis.

6. The device as recited in claim 1 wherein said cosmetic agent is selected from the group consisting of lidocaine, acetic acid, vitamin A, retinyl palmitate, tocopheryl acetate, tocopherol, glucoside, and mandelic acid.

7. The device as recited in claim 1 further comprising a plurality of slits on said substrate and further comprising a release liner which is removable from said mask.

\* \* \* \* \*